United States Patent [19]

Barbour et al.

[11] Patent Number: 5,071,771

[45] Date of Patent: Dec. 10, 1991

[54] IDENTIFICATION OF WOOD SPECIES

[75] Inventors: R. James Barbour, Russell; Ludmila L. Danylewych-May, North York; Roger Sutcliffe, Nepean, all of Canada

[73] Assignee: Forintek Canada Corporation, Vancouver, Canada

[21] Appl. No.: 444,878

[22] Filed: Dec. 4, 1989

[51] Int. Cl.[5] ............................................. G01N 21/71
[52] U.S. Cl. ................................... 436/153; 250/282; 250/287
[58] Field of Search .................. 436/153; 250/287, 282

[56] References Cited

U.S. PATENT DOCUMENTS 4,000,406  1/1988  Wohltjen ............................ 436/153
4,551,624  12/1985  Spangler et al. ..................... 250/287

OTHER PUBLICATIONS

Journal of Wood Chemistry and Tech. 3(4), 377–397 (1983) John R. Obst.
Rapid Characterization of Wood Species by Ion Mobility Spectrometer, A. H. Lawrence-Published Feb. 2, 1989 at 75th Annual Meeting of the Technical Section of the C.P.P.A.
Abstract–Use of Ion Mobility Spectrometry for Rapid Identification of Wood Species by R. J. Barbour & A. H. Lawrence, Jun. 19-22, 1988–42nd Annual Meeting of the Forest Products Research Society in Quebec, Canada.
Textbook of Wood Technology, Third Edition, published by McGraw-Hill, Authors: A. J. Panshin & Carl De Zeeow, pp. 419 to 421.

*Primary Examiner*—Robert J. Warden
*Assistant Examiner*—Laura E. Collins
*Attorney, Agent, or Firm*—William H. James

[57] ABSTRACT

A method and apparatus to produce an ion mobility signature representing a wood sample provides a method of comparing signatures to identify the species of the wood sample. A method of producing an ion drift time signature representing a wood species comprises heating at least a portion of a wood sample at a temperature in the range of about 220° to 350° C. to desorb and produce trace vapors from the wood sample, ionize the trace vapors at a temperature in the range of about 220° to 350° C., pulse ions through a gate into a drift region, measure the time of arrival of the ions and the ion flux for each pulse, with a collector electrode, located at the end of the drift region to produce an ionic signal, and amplify and average the ionic signal to provide an ion drift time signature for the wood sample.

20 Claims, 7 Drawing Sheets

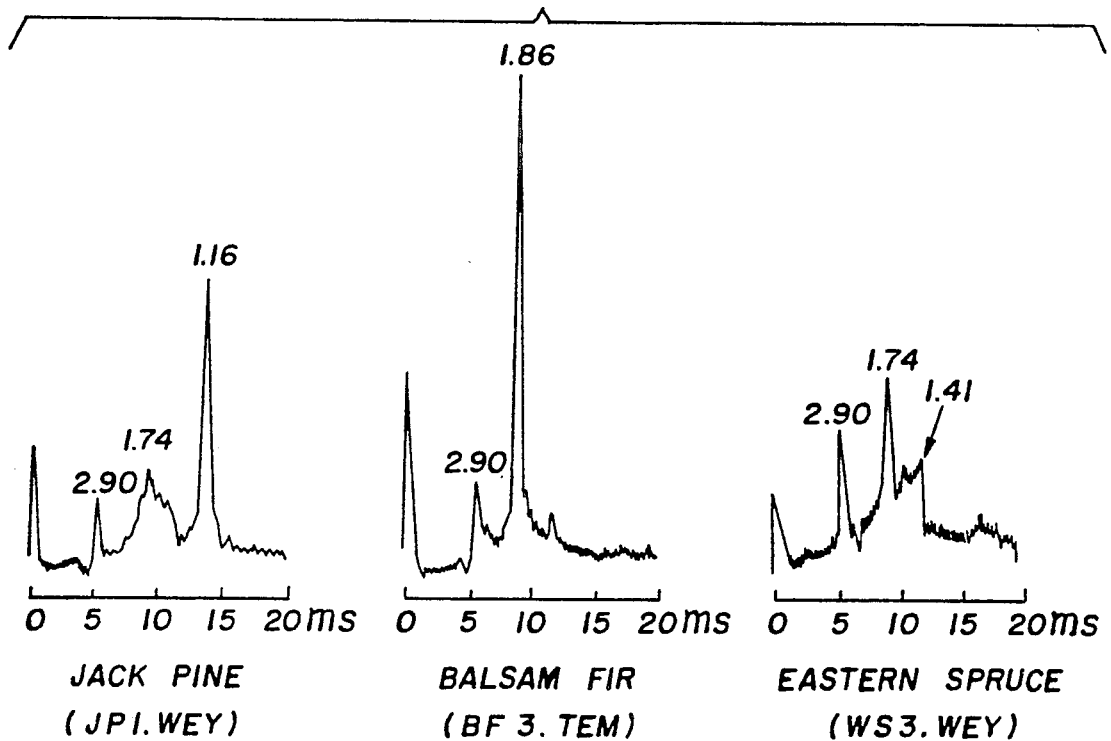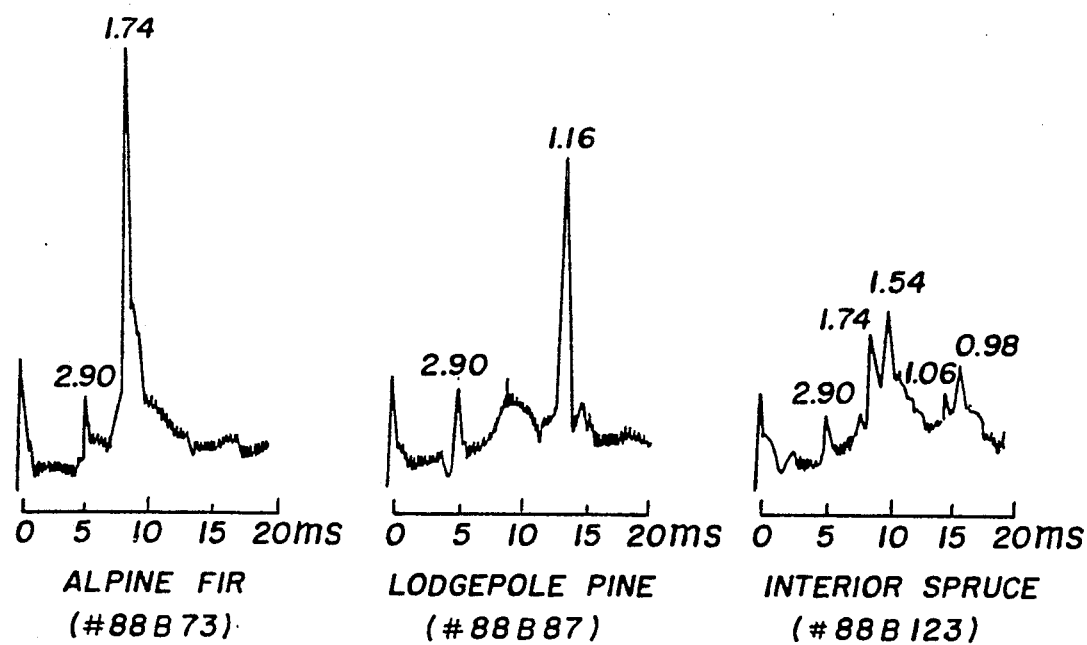
Fig. 2.

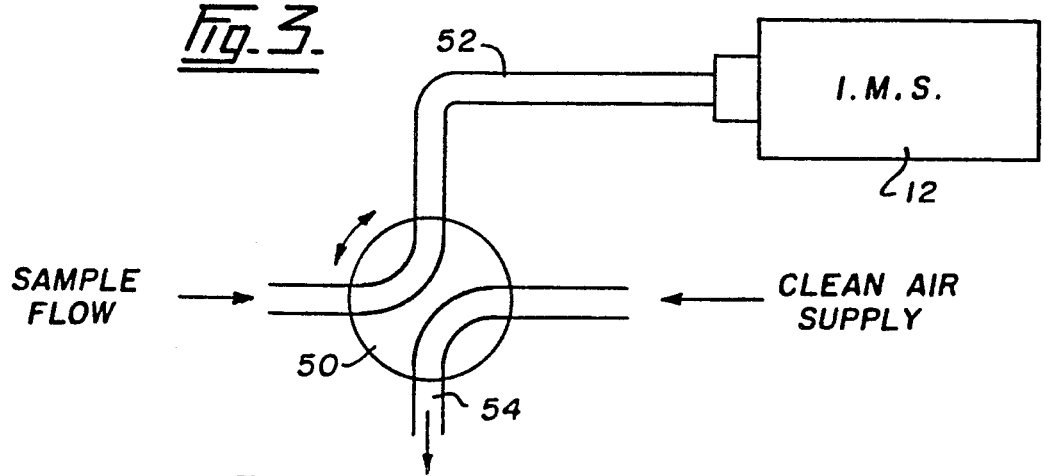
Fig. 3.
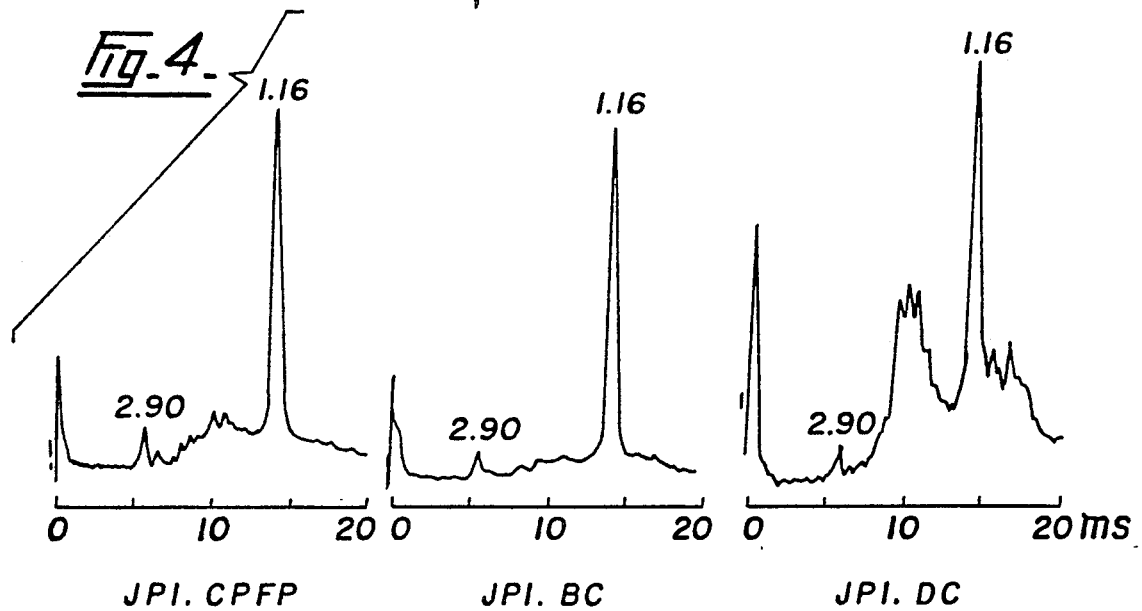
Fig. 4.
JPI. CPFP    JPI. BC    JPI. DC
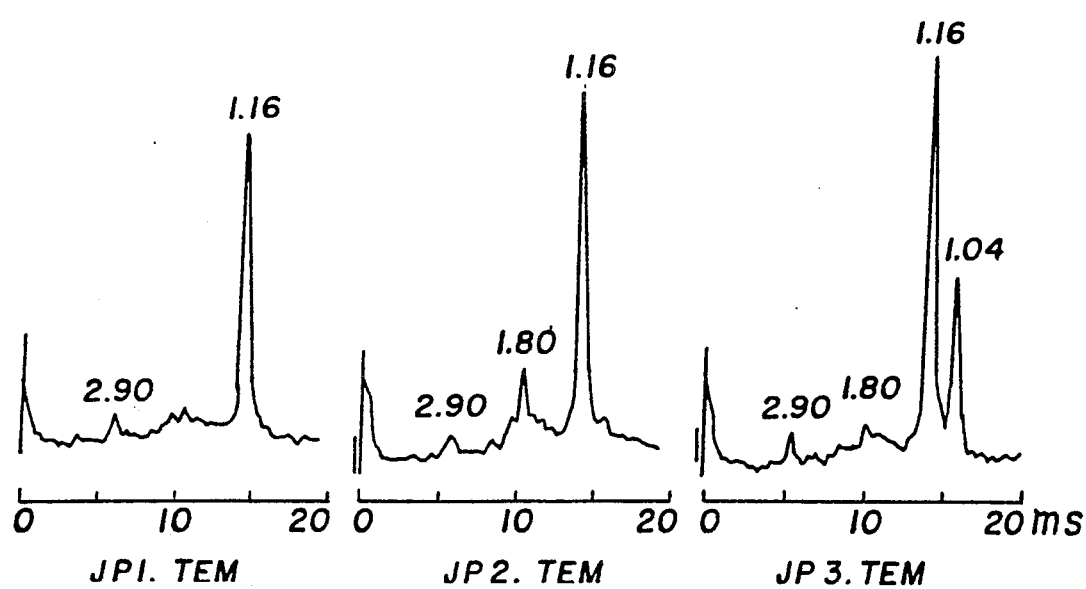
JPI. TEM    JP2. TEM    JP3. TEM

Fig. 6.
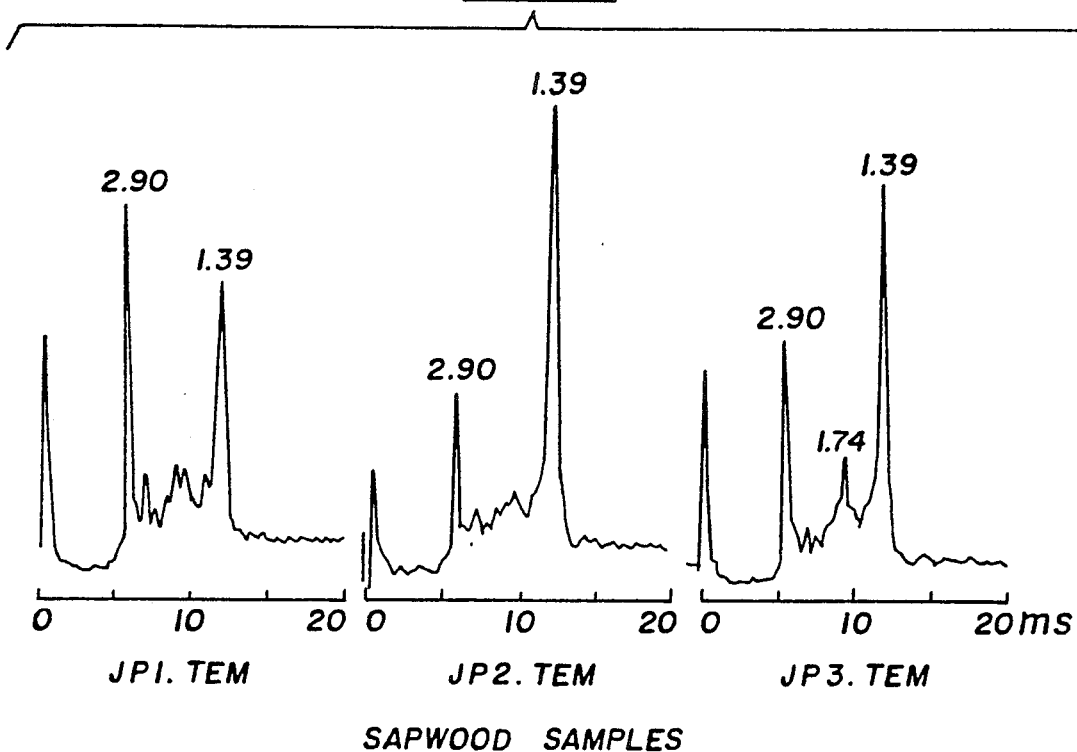
SAPWOOD SAMPLES
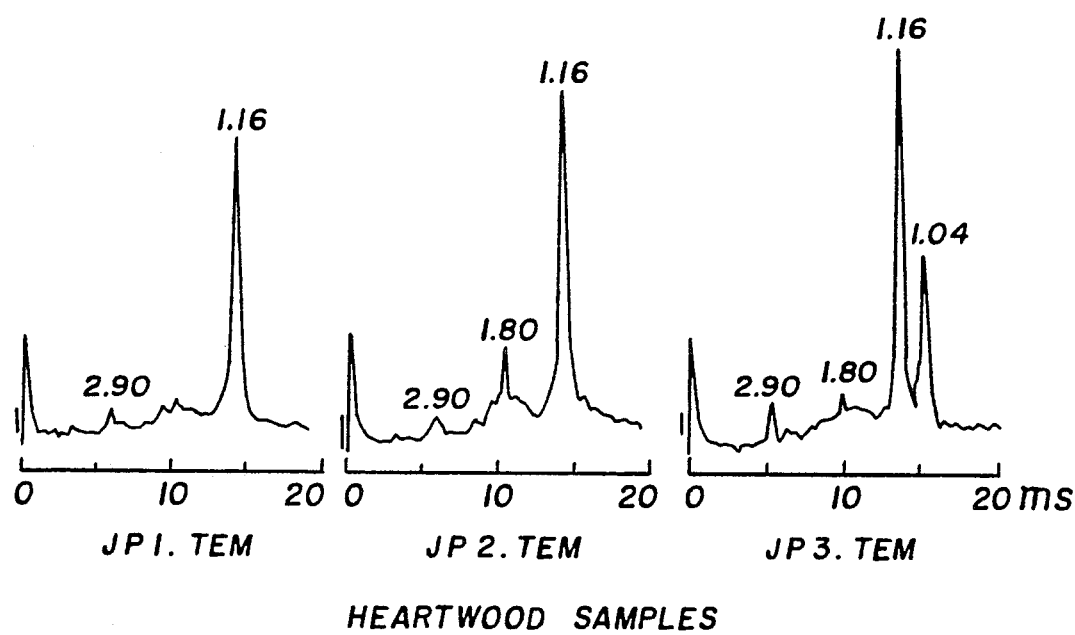
HEARTWOOD SAMPLES

Fig. 8.
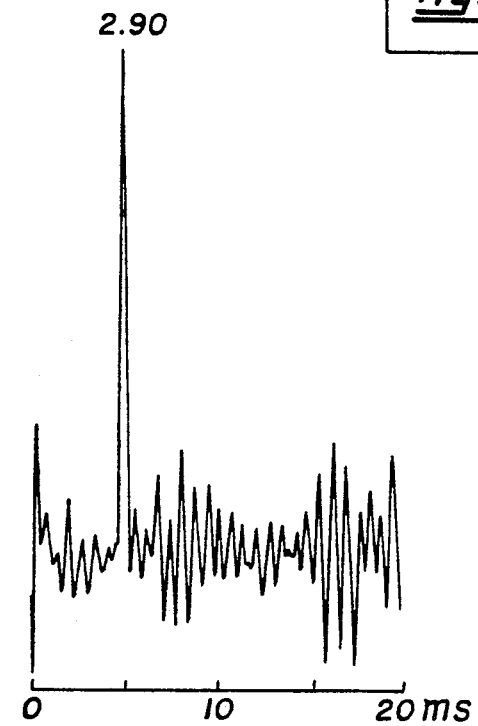
TRACE 1 - BACKGROUND
WITH ACOUSTICAL COVER OFF
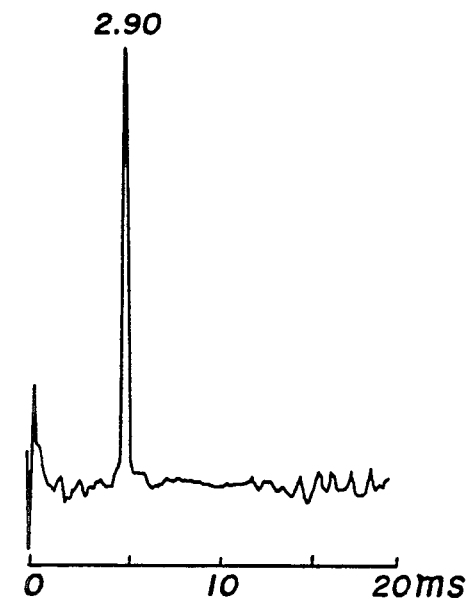
TRACE 2 - BACKGROUND
WITH ACOUSTICAL COVER ON
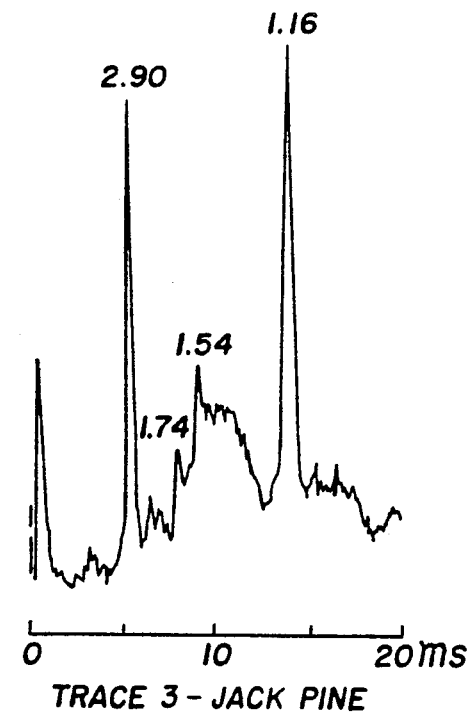
TRACE 3 - JACK PINE
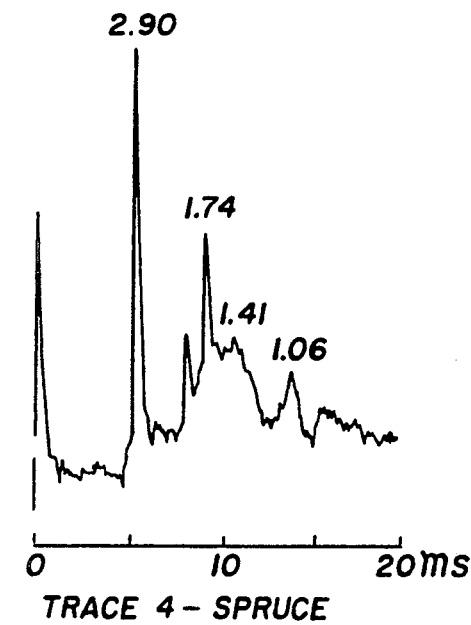
TRACE 4 - SPRUCE

IDENTIFICATION OF WOOD SPECIES

BACKGROUND OF THE INVENTION

The present invention relates to sampling wood to identify wood species. More specifically the present invention provides a method of producing an ion mobility signature representing a wood sample and then comparing the signature with known signatures of wood species to determine the wood species of the sample.

When logs arrive at saw mills they are usually stacked, and in many cases it is difficult to tell the species of a specific log. It is known that different types of wood species have different commercial values and thus there is often an advantage for the saw mills to sort out different wood species in order to maximize the values of the more valuable woods. Today, distinguishing one species of wood from another is often done manually either in log form or when lumber is sorted, and this is not necessarily the most reliable or economical method. Once the species of the wood has been determined, there is generally a decision time of about 2 to 10 seconds while the wood moves along a conveyor to a position where the wood is sorted into a different species.

Ion mobility spectrometry (IMS) is recent technology which separates ionized compounds based on differences in their drift velocity through a gas under an applied electric field. This technique has the ability to produce a characteristic spectrum of the series of high molecular weight compounds in a matter of milliseconds. It is known that it can produce identifiable signatures for such items as drugs and explosives and is being developed for use by customs, airlines and police forces to detect such substances. Initial tests were carried out to determine if IMS could be used to identify different wood species. A report on these tests was published by A. H. Lawrence on Feb. 2, 1989 at the 75th annual meeting of the Technical Section of the Canadian Pulp and Paper Association entitled "Rapid Characterization of Wood Species by Ion Mobility Spectrometry". Some tests were carried out in the "positive mode" and some in the "negative mode". Positive mode is when polarity of the electric field is positive, i.e. positive ions present in the detection mode. Negative mode is when the polarity of the electric field is negative, i.e. negative ions present in the detection mode. The initial tests showed that some wood species could be identified one from the other provided the tests were conducted in both modes. However, there were a number of variable parameters that did not initially appear to be acceptable for use in the lumber industry. First of all sampling and analyzing by an IMS device took several seconds and this would hardly be feasible for fast moving conveyors used in saw mills. Secondly it seemed that only certain types of wood species could be identified and thirdly it was not clear how such a piece of equipment would work in a saw mill environment with saw dust, other types of particles as well as vapours from both machinery and wood are present.

Ion mobility spectrometers are known, and it is also known that specimens analyzed by such a spectrometer can produce different signatures, or plasmagrams as they are sometimes referred to, which are affected by many different variables, e.g. temperature, barometric pressure, humidity, etc. Furthermore, when one analyzes a specimen of wood, the wood may be dry or moist. Heartwood and sapwood from the same wood species have different ion mobility signatures, and there are other effects such as extraneous noises, radio signals, vibrations etc. that may effect the signature of a trace sample.

SUMMARY OF THE INVENTION

We have now found that by desorbing wood within a preferred temperature range to produce trace vapours, and ionizing the trace vapours at a further preferred temperature range, we can measure the time of arrival of the ions and the ion flux at a collector electrode and produce a weak electric current signal representing an ionic signal. The measurement can be made in the negative mode and the positive mode and different signals are produced in the two modes. Mobility of an ion is dependent at least partly, on the mass and shape of the ion, as well as the charge distribution. Mobilities are influenced by the media through which the ions travel, and by gas density variations which in turn depend on gas temperature and pressures. The density variations can be normalized by reducing the mobility to a standard temperature and pressure and thus produce a reduced ion mobility signature derived from the ion drift time signature for that particular wood species. It has been found that these different signatures can be used to identify most wood species regardless of the fact that the temperature, and pressure conditions vary for different locations. The signatures are identifiable regardless of the moisture content of the wood, and regardless of environmental conditions. Heartwood and sapwood signatures for the same wood species are different, but are specific for that species.

One aim of the present invention is to be able to analyze a wood sample within a short space of time, and detect the wood species in less than a second. To achieve this time and to repeat identifying different wood specimens, more than one apparatus may be required. Furthermore, under some conditions such as analyzing a cold wood sample, then longer times are necessary. It is a further aim to provide a sampling arrangement that works in the environment of a saw mill under conditions where saw dust and other dust is blowing about under extreme noise and vibration conditions, and still produce a signature so the wood species can be identified.

The present invention provides a method of producing an ion drift time signature representing a wood species, comprising the steps of, heating at least a portion of a wood sample at a temperature in the range of about 220° to 350° C. to desorb and produce trace vapours from the wood sample; ionizing the trace vapours in an ionizing zone at a temperature in the range of 220° to 350° C.; pulsing ions from the ionizing zone through a gate means into a drift region; measuring the time of arrival of the ions and the ion flux, for each pulse, with a collector electrode located at the end of the drift region to produce an ionic signal, and amplifying and averaging the ionic signal to provide an ion drift time signature for the wood sample.

There is further provided a method of identifying a wood species comprising the steps of heating at least a portion of a wood sample at a temperature in the range of about 220° to 350° C. to desorb and produce trace vapours from the wood sample; ionizing the trace vapours in an ionizing zone at a temperature in the range of about 220° to 350° C.; determining drift time of ions and ion flux produced in the ionizing zone, at a collector electrode spaced from the ionizing zone, to produce an ionic signal; amplifying and averaging the ionic signal to provide an ion drift time signature for the wood sample, and comparing the signature with known wood species signatures to determine the wood species of the wood sample.

In another embodiment there is also provided an apparatus for producing an ion drift time representing a wood species from a wood sample comprising heating means to heat at least a portion of the wood sample to a temperature in the range of about 220° to 350° C. to desorb and produce trace vapours from the wood sample; gas flow means for transferring the trace vapours to an ionizing zone, the ionizing zone being at a temperature in the range of about 220° to 350° C.; means to ionize the trace vapours in the ionizing zone; gate means adjacent the ionizing zone leading to a drift region having a collector electrode at the other side from the gate means, the collector electrode adapted to determine drift time of ions and ion flux in the drift region, and amplification means and averaging means to provide an ion drift time signature for the wood sample.

BRIEF DESCRIPTION OF THE DRAWINGS

In drawings which illustrate embodiments of the invention,

FIG. 2 show six ion mobility signatures for different wood species.

FIG. 3 is a schematic diagram for air carrier flow and purge flow for the IMS and sample line.

FIG. 4 show six ion mobility signatures for different samples of jack pine showing the reproducibility of the signatures.

FIG. 6 show ion mobility signatures showing the difference between sapwood and heartwood for jack pine.

FIG. 8 show ion mobility signatures at chipper and canter sites with an acoustical cover on and off.

DETAILED DESCRIPTION OF THE INVENTION

Figure 1:
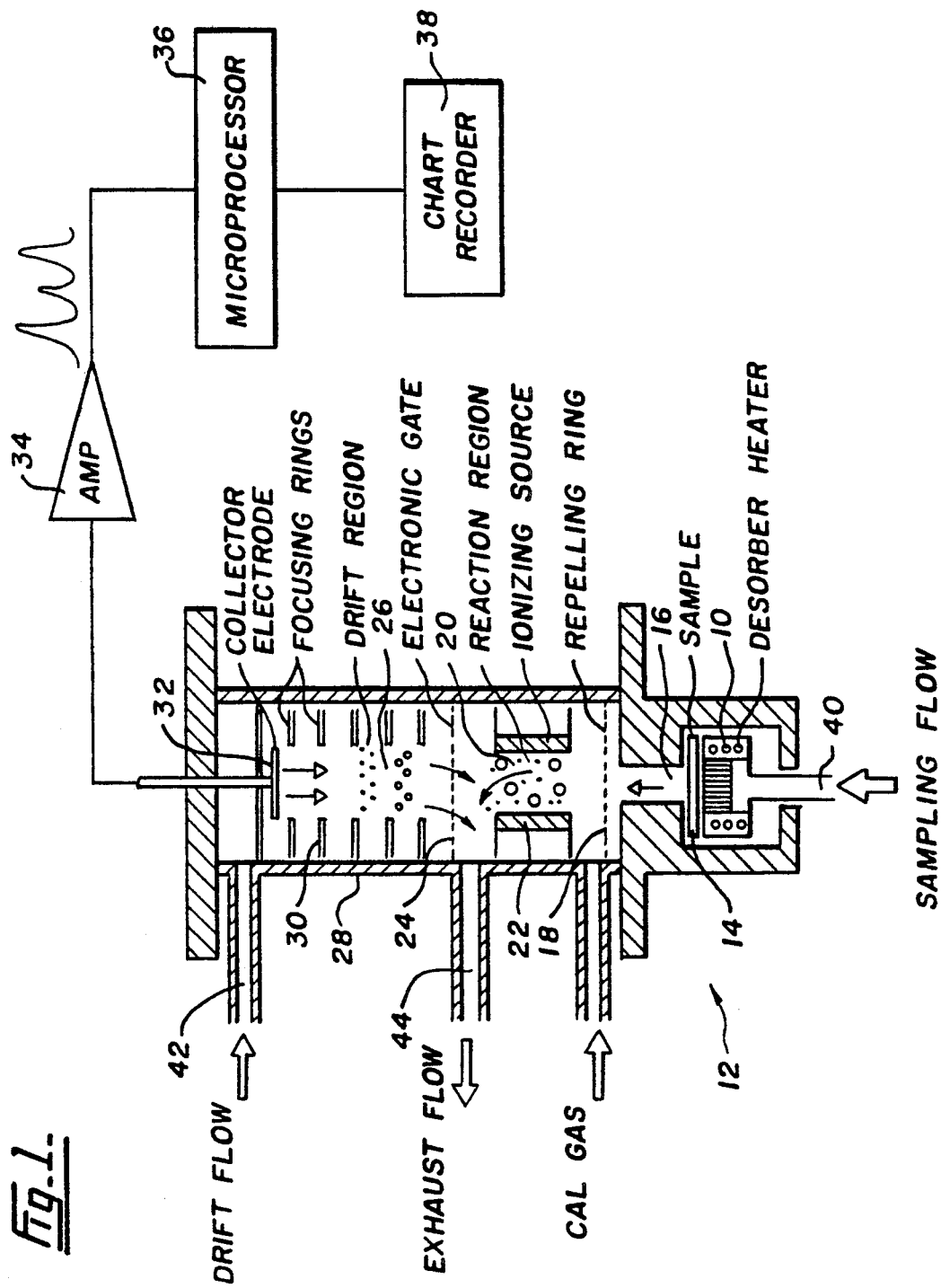
FIG. 1 is a schematic diagram showing an ion mobility spectrometer suitable for analyzing a wood sample according to the present invention.

An ion mobility spectrometer (IMS) is illustrated in FIG. 1. For the purposes of experimentation a unit manufactured by Barringer Research Limited was modified for sampling wood. A desorber heater 10 is positioned at one end of a spectrometer 12 and a wood sample 14 rests on top of a filter above the desorber heater 10. A passage 16 from the desorber heater leads through a repelling ring 18 to an ionizing zone 20 which includes a weak radioactive source. An electronic gate 24 separates the ionizing zone 20 from a drift region 26. The drift region is a drift tube 28 with a series of stacked cylindrical guard rings 30 to produce a uniform electric field throughout the drift region 26. A collector electrode 32 at the top of the drift region 26 measures the drift time of the ions and also the ion flux. The electrode 32 produces a weak electric current which is an ionic signal. This signal is amplified by amplifier 34 then averaged by a signal averager 36 before being recorded on a chart recorder 38 as a representative ion mobility signature for the wood sample 14. A Nicolet signal averager was used for test purposes, however, intregated averagers are used for saw mill operations.

A sampling gas flow 40 collects trace vapours from the wood sample 14, and transfers the vapours through a transfer line 16, in the test machine into the ionizing zone 20. The transfer lines 16 containing the trace vapours are heated to prevent condensation of the trace vapour. The entire cell is at atmospheric pressure and the ionizing source, which in one embodiment is $Ni^{63}$, a radioactive isotope, generates certain reactant ions. These ionize a fraction of the trace sample molecules in the sampling gas flow. As a result of a complex interchange reaction which takes place in the of a spectrometer 12 and a wood sample 14 rests on top of a filter above the desorber heater 10. A passage 16 from the desorber heater leads through a repelling ring 18 to an ionizing zone 20 which includes a weak radioactive source. An electronic gate 24 separates the ionizing zone 20 from a drift region 26. The drift region is a drift tube 28 with a series of stacked cylindrical guard rings 30 to produce a uniform electric field throughout the drift region 26. A collector electrode 32 at the top of the drift region 26 measures the drift time of the ions and also the ion flux. The electrode 32 produces a weak electric current which is an ionic signal. This signal is amplified by amplifier 34 then averaged by a signal averager 36 before being recorded on a chart recorder 38 as a representative ion mobility signature for the wood sample 14. A Nicolet signal averager was used for test purposes, however, integrated averagers are used for saw mill operations.

A sampling gas flow 40 collects trace vapours from the wood sample 14, and transfers the vapours through a transfer line 16, in the test machine into the ionizing zone 20. The transfer lines 16 containing the trace vapours are heated to prevent condensation of the trace vapour. The entire cell is at atmospheric pressure and the ionizing source, which in one embodiment is $Ni^{63}$, a radioactive isotope, generates certain reactant ions. These ionize a fraction of the trace sample molecules in the sampling gas flow. As a result of a complex interchange reaction which takes place in the ionizing zone, the molecules of certain species of trace vapours form ions while others do not. These ions are prevented from entering the drift region 26 by the electronic gate 24 and cannot return to the passageway 16 because of the repelling ring 18. When the gate 24 is open, the ions accelerate under the influence of a strong electric field through the drift region 26 towards the collector electrode 32. The gate 24 is repetitively opened at brief intervals (typically 0.2 milliseconds) emitting pulses of mixed ions into the drift region 26. A typical time between pulses is 20 milliseconds. As they pulse, the ions in any particular pulse separate into their individual chemical species based upon their differing intrinsic mobilities. The arrival of the individual ion pulses at the collector electrode 32 produces a characteristic ion arrival time spectrum. This ionic signal in the form of a weak electric current from the collector electrode 32 is amplified and then fed to the Nicolet signal averager where it is filtered, digitized and stacked to increase signal to noise ratio. The number of sweeps or cycles can be varied and the average signal is viewed on a screen in real time and subsequently displayed on the chart recorder 38. Because each ion travels at different velocities, the ions are separated in drift time as they arrive at the collector electrode 32. A plot of ion inten- -continued

WOOD SPECIES ANALYSED WITH BARRING IMS DETECTOR

| SPECIES GROUP | SPECIES | IMS SIGNATURE $K_0(cm^2/V \cdot s)$ |
|---|---|---|
| | White Pine | 1.16(s); 1.74; 1.54; 1.41 |
| Western Interior | Western Larch | 1.60(s); 1.74; 1.51 |
| | Lodgepole Pine | 1.74(s); 1.16(s) |
| | Douglas-Fir | 1.60(s); 1.74; 1.48 |
| | Alpine Fir | 1.86(s); 1.74(s) |
| | Interior Spruce | 1.74(s); 0.98 |
| | Western Hemlock (interior samples) | 1.86(s); 1.74(s); 1.48; 1.24; 1.62 |
| Western Coastal | Sitka Spruce | 1.41(s); 2.26; 1.06 |
| | Douglas-Fir | 1.60(s); 1.74; 1.48 |
| | Western Hemlock (costal samples) | 1.39(s); 1.74 |
| | Amabilis Fir | 1.74(s); 1.41 |
| | Alpine Fir | 1.86(s); 1.74 |

(s) denotes the most prominent io peak in the plasmagram

Table 1 illustrates the wood species analyzed with the IMS detector. The signatures for the reduced ion mobility figures (Ko) are shown for the different wood species and also possible conflicts within the groups. The groups are selected for ones that grow in different areas and therefore are not likely to be mixed up in a mill. The most prominent peaks in the signatures are the distinguishing features of the signature.

Figure 5:
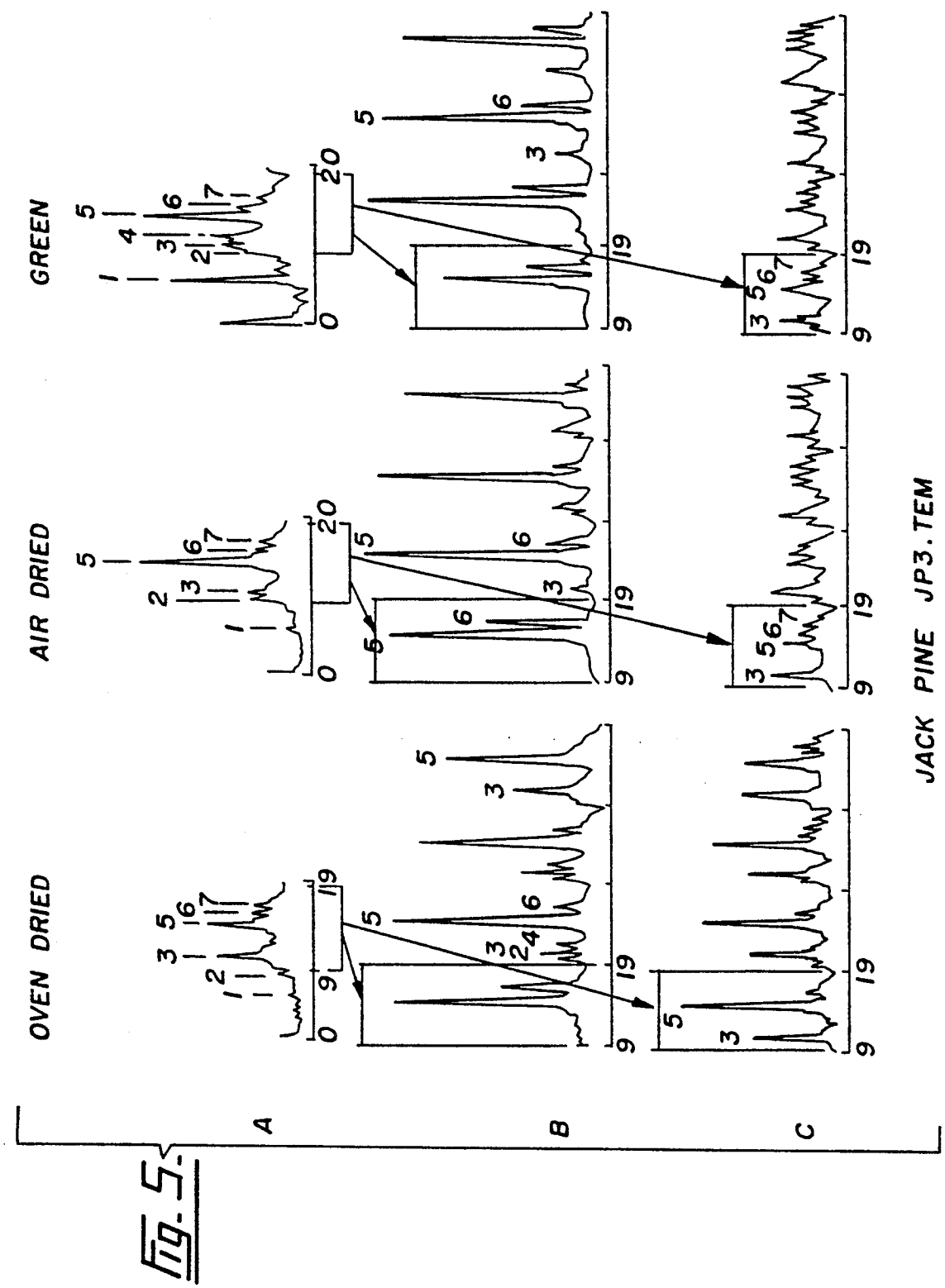
FIG. 5 show ion mobility signatures showing the effects of variable moisture content for jack pine.

The effects of variable moisture content are illustrated in FIG. 5. Wood samples in different states of drying were investigated. Jack pine in three different moisture conditions was analyzed, the green sample contains a higher percentage of moisture than the air dried sample. However, the signatures differ only in the time required to heat the sample to a high enough temperature for the plasmagram to develop. Traces B and C in FIG. 5 show 10 ms segments of the signature A expanded in four consecutive analysis time slots of 0.64 seconds. There is little difference between the signatures for the three samples thus the moisture content does not modify the appearance of the signature provided the sample is heated to the required desorption temperature preferably 300° C. Similar tests were carried out with balsam fir with similar results. This means that IMS can be used anywhere in the sequence of processing wood products, even after the wood has been dried.

Sapwood samples and heartwood samples were taken from jack pine and analyzed. The signatures, as shown in FIG. 6, indicate that the sapwood samples contain a strong peak of reduced mobility of 1.39 $K_o$. For the heartwood samples a 1.16 $K_o$ peak occurs and it is clear that the signatures for heartwood and sapwood within the same species are reproducible but differ one from the other. Other species of wood were looked at with similar results.

Figure 7:
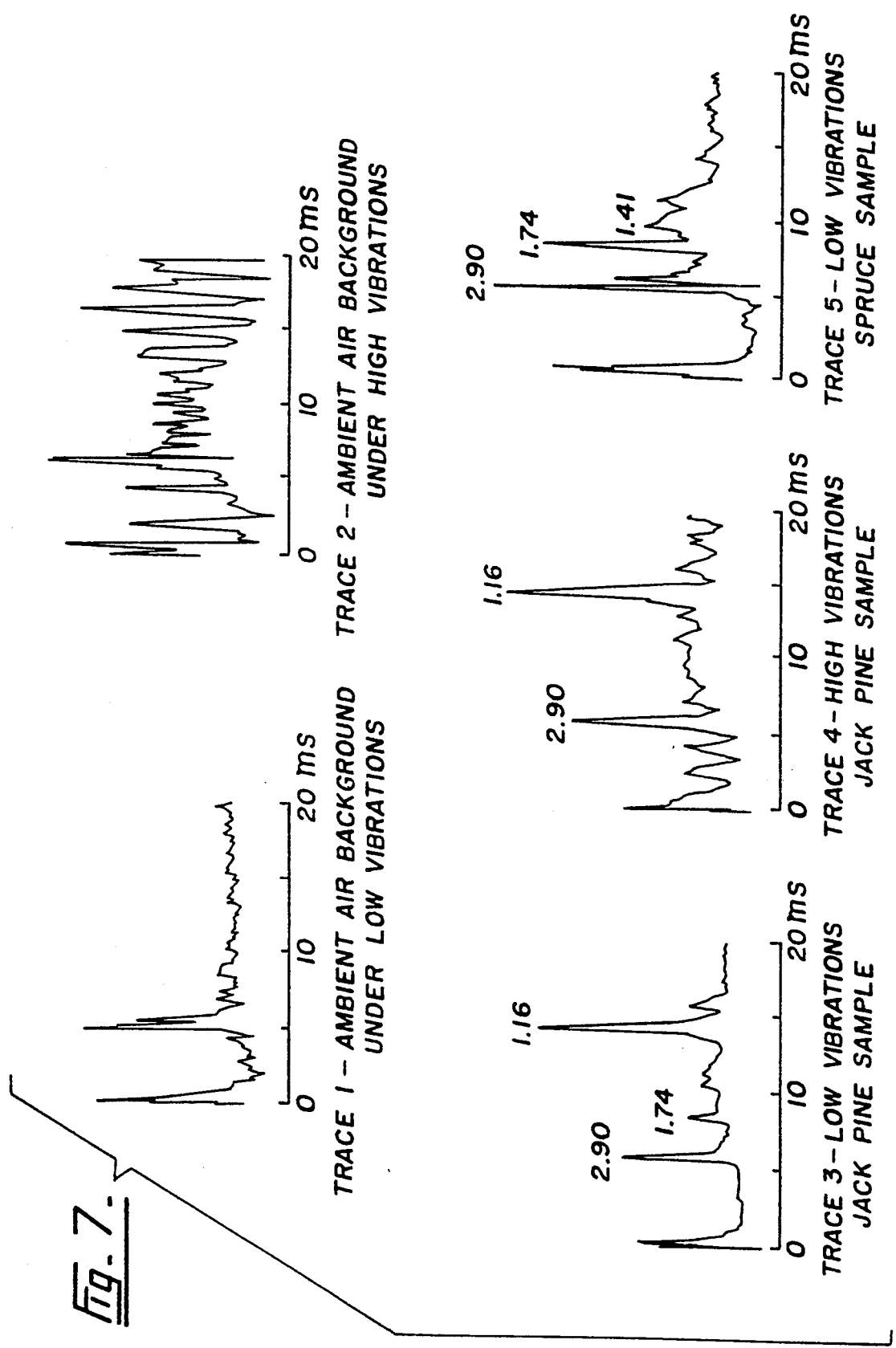
FIG. 7 show ion mobility signatures at tree loading sites under both low and high vibrations.

In order to assess the feasibility of an IMS installation in the field, tests were conducted at a tree loading site and the equipment was set up in an area where tree lengths are loaded on conveyors to be sent to a debarker. Large amplitude shocks were experienced and vibration signals were picked up by the IMS detector as shown in FIG. 7. Tests were also conducted at six additional locations in a saw mill.

These locations were chosen as suitable positions in the saw mill where the logs or lumber could be sorted dependent upon wood species, and conveyed to different areas. The locations took into account the different environmental conditions in the mill.

Throughout the mill testing, ambient air was used without predrying or filtering for the sample carrier flow. The ambient air was coarsely filtered and partially dried for the drift gas flow. No additional background peaks were observed from the ambient air, as illustrated in trace 1 of FIG. 7, and no chemical interference was detected. Acoustic and vibration effects from falling and bumping trees were severe as can be seen in trace 2. Traces 3 and 4 are the signatures from jack pine samples from the mill run at low and high vibration noise and trace 5 is a sample of spruce run under low vibrational noise. In both cases positive detection and identification is evident.

Further tests were conducted at a chipper and canter site where many electric motors were generally running continuously. The hydraulic system was intermittent and settled wood dust was present on all surfaces. The air was estimated to contain about 100 particles per cubic foot. Vibration noise was low with only occasional shocks as logs were fed into the conveyor, however, acoustical noise levels were severe as shown in FIG. 8. Traces 1 and 2 show the background signatures before and after an acoustical protection cover was placed on the IMS system. Traces 3 and 4 show the signatures of jack pine and spruce on this site. Both the jack pine and spruce samples were reliably detected.

The 2.90 $K_o$ peak in FIG. 8 represents the partially hydrated chloride ion, $(H_2O)_nCl^-$, which is present in the reaction region and ion mixture allowed into the drift region. In a preferred embodiment in the negative mode, chloride reactant ions are generated in the reaction region from chlorinated compounds, typically methylene chloride (dichloromethane), introduced as a dopant into the sample carrier gas. Under the usual operating conditions these are partially hydrated, resulting in the reduced mobility constant of 2.90 $cm^2/Vs$. Upon introduction of sample molecules into the reaction region, analyte ions are formed at the expense of the chloride ions, and the reactant ion concentration decreases and may become even completely depleted.

Other reactant ions that may be used as indicators are bromides and iodides in the negative mode, and nicotinamide in the positive mode.

In certain locations acoustical protectors either in the form of an acoustical cover or by utilizing electronic circuits are provided to eliminate extraneous noise from vibrations and other spurious electronic signals which are often present in industrial locations.

The tests have shown that there is an unambiguous signature for different wood species. Furthermore, the IMS application can handle wood with moisture contents varying from about 0 to 200%. The machine can operate with mill background atmosphere and in a mill environment. For the purposes of the test sampling was conducted with saw dust, however, other types of sampling may be developed.

Various changes may be made to the embodiments described herein without departing from the scope of the present invention which is limited only by the following claims.

The embodiments of the present invention in which an exclusive property or privilege is claimed are defined as follows:

1. A method of producing an ion drift time signature representing a wood species, comprising the steps of heating at least a portion of a wood sample at a temperature in the range of about 220° to 350° C. to desorb and produce trace vapours from the wood sample;

ionizing the trace vapours in an ionizing zone at a temperature in the range of about 220° to 350° C.;

pulsing ions from the ionizing zone through a gate means into a drift region;

measuring the time of arrival of the ions and the ion flux, for each pulse, with a collector electrode located at the end of the drift region to produce an ionic signal, and amplifying and averaging the ionic signal to provide an ion drift time signature for the wood sample.

2. The method of producing a signature representing a wood species according to claim 1 wherein the wood sample is heated to a temperature in the range of about 250° to 315° C.

3. The method of producing a signature representing a wood species according to claim 1 wherein the ionizing zone is at a temperature in the range of about 230° to 250° C.

4. The method of producing a signature representing a wood species according to claim 1 wherein the measuring of the ions in the drift region occurs in a negative mode.

5. The method of producing a signature representing a wood species according to claim 1 wherein the wood sample is heated to a temperature in the range of about 250° to 315° C., and the measuring of the ions in the drift region occurs in a negative mode.

6. The method of producing a signature representing a wood species according to claim 1 wherein the ion drift time signature of the wood sample is reduced to form a reduced ion mobility signature of the wood sample.

7. The method of producing a signature representing a wood species according to claim 1 including a sampling gas flow for transmitting the trace vapours to the ionizing zone.

8. The method of producing a signature representing a wood species according to claim 7 wherein the sampling gas is ambient air.

9. The method of producing a signature representing a wood species according to claim 1 including a drift gas flow through the drift region from the collector electrode towards the ionizing zone.

10. The method of producing a signature representing a wood species according to claim 9 wherein the drift gas is ambient air.

11. The method of producing a signature representing a wood species according to claim 1 wherein an ion drift time signature of the wood sample is provided within a time of 0.3 seconds.

12. The method of producing a signature representing a wood species according to claim 1 wherein the wood sample is preheated before carrying out the steps of producing an ion drift signature.

13. The method of producing a signature representing a wood species according to claim 1 wherein the ionizing zone is purged following a detection cycle.

14. The method of producing a signature representing a wood species according to claim 13 wherein the ionizing zone is purged by clean ambient air.

15. The method of producing a signature representing a wood species according to claim 1 wherein an ion drift time signature of the wood sample is produced in a time range of about every 1.5 to 5 seconds.

16. The method of producing a signature representing a wood species according to claim 1 including a reactant ion present in the drift region.

17. The method of producing a signature representing a wood species according to claim 16 wherein the measuring of the ions occurs in the negative mode and the reactant ion is hydrated chloride.

18. A method of identifying a wood species comprising the steps of:

heating at least a portion of a wood sample at a temperature in the range of about 220° to 350° C. to desorb and produce trace vapours from the wood sample;

ionizing the trace vapours in an ionizing zone at a temperature in the range of about 220° to 350° C.;

determining drift time of ions and ion flux produced in the ionizing zone, at a collector electrode spaced from the ionizing zone, to produce an ionic signal;

amplifying and averaging the ionic signal to provide an ion drift time signature for the wood sample, and comparing the signature with known wood species signatures to determine wood species of the wood sample.

19. The method of identifying a wood species according to claim 18 wherein the ion drift time signature is a reduced ion mobility signature.

20. The method of identifying a wood species according to claim 18, wherein the wood sample is heated to a temperature in the range of about 250° to 315° C., and measuring of the ions in the drift region occures in a negative mode.

* * * * *